United States Patent [19]

Young et al.

[11] Patent Number: 5,136,034

[45] Date of Patent: Aug. 4, 1992

[54] SYNTHESIS OF CHIRAL THIOACETALS AND THIOETHERS

[75] Inventors: Robert N. Young, Senneville; Michel Thérien, Montreal; Jacques-Yves Gauthier, Laval; Robert Zamboni, Longueuil; Michel L. Belley, St. Laurent, all of Canada

[73] Assignee: Merck Frosst Canada, Inc., Kirkland, Canada

[21] Appl. No.: 593,836

[22] Filed: Oct. 5, 1990

Related U.S. Application Data

[63] Continuation of Ser. No. 306,616, Feb. 6, 1989, abandoned, which is a continuation of Ser. No. 11,166, Feb. 5, 1987, abandoned.

[51] Int. Cl.$^5$ ............... C07D 209/00; C07D 215/36; C07D 215/16; C07D 215/38
[52] U.S. Cl. .......................................... 544/3; 544/54; 544/55; 544/56; 544/62; 544/63; 544/96; 546/153; 546/155; 546/156; 546/157; 546/159; 546/160; 546/168; 546/170; 546/171; 546/172
[58] Field of Search ............... 546/153, 155, 156, 157, 546/159, 160, 168, 170, 171, 172, 175; 544/3, 54, 55, 56, 62, 63, 96

[56] References Cited

U.S. PATENT DOCUMENTS 4,598,150  7/1986  Fujisaki et al. .................. 546/153
4,661,499  4/1987  Young et al. ..................... 546/153

Primary Examiner—C. Warren Ivy
Assistant Examiner—Raymond Covington
Attorney, Agent, or Firm—Gabriel Lopez; Joseph F. DiPrima

[57] ABSTRACT

Thioacids, thiols, an acid, and an aldehyde are used to produce chiral thioacetals of the general formula.

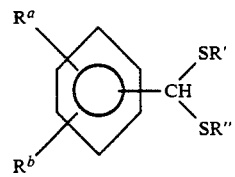

The compounds are leukotriene antagonists.

2 Claims, No Drawings

SYNTHESIS OF CHIRAL THIOACETALS AND THIOETHERS

CROSS REFERENCE

This is a continuation of U.S. Ser. No. 306,616, Feb. 6, 1989, abandoned, which is a continuation of U.S. Ser. No. 011,166, Feb. 5, 1987, abandoned.

2-substituted quinoline dioic acids of Formula B are described in U.S. Pat. No. 4,851,409, which is incorporated herein by reference.

BACKGROUND

Various chiral, or unsymmetrical, thioacetals have been described which have useful pharmaceutical properties as leukotriene antagonists The synthesis of these compounds has heretofore involved the production primarily of symmetric analogs, followed by separation of the desired chiral, or unsymmetric compounds.

SUMMARY OF THE INVENTION

A synthesis has now been found which produces chiral thioacetals or thioethers as major components. This synthesis also advantageously permits the resolution of an intermediate into its opitical isomers, thus leading to the direct synthesis of resolved end products.

DETAILED DESCRIPTION

The chiral thioacetals of Formula I are prepared by the reaction of a thioacid, a thiol and an acid with an alkyl- or arylaldehyde, followed by reaction with a reactive electrophile according to the following general scheme:

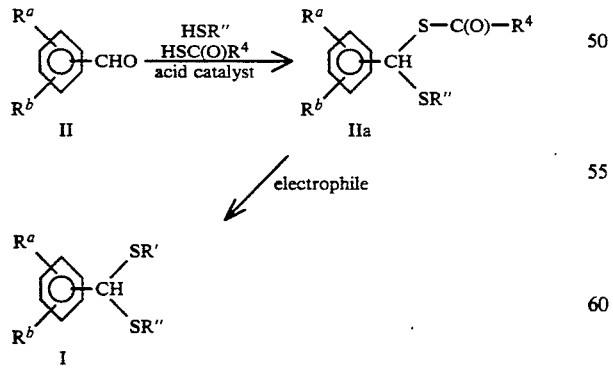

The first step of this synthesis produces the first unsymmetric thio compound almost exclusively. The selection of the appropriate electrophile for the second step affords the end product I of choice, Oxidation of I yields the sulfoxide and sulfone compounds of Formulae B and C.

This synthesis not only produces chiral compound I in high yield by a simplified route but, when $R^4$ above is chiral, resolution of III into its optical isomers, permits the direct synthesis of resolved forms of compound I by reacting either isomer with an appropriate electrophile.

An embodiment of the compounds of Formula I are the 2-substituted quinoline dioic acids of Formula B:

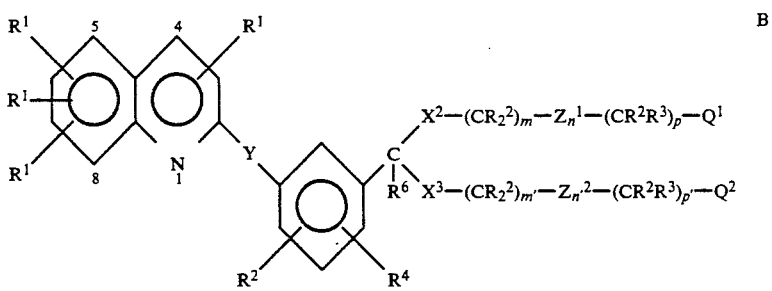

where
$R^1$ is H, halogen, $C_1$-$C_8$ alkyl, $C_2$-$C_8$ alkenyl, $C_2$-$C_8$ alkyn , —$CF_3$, —$OR^2$, —$SR^2$, —$S(O)R^2$, —$S(O)_2R^2$, —$NR^2R^2$, —CHO, —$COOR^2$, —C(=O)$R^2$, —C(OH)$R^2R^2$, —CN, —$NO_2$, substituted or unsubstituted phenyl, substituted or unsubstituted benzyl, or substituted or unsubstituted phenethyl;

$R^2$ is H, $C_1$-$C_8$ alkyl, $C_2$-$C_8$ alkenyl, $C_2$-$C_8$ alkynyl, —$CF_3$, substituted or unsubstituted phenyl, substituted or unsubstituted benzyl, or substituted or unsubstituted phenethyl;

$R^3$ is H, halogen, —$NO_2$, —CN, —$OR^2$, —$SR^2$, or $C_1$-$C_8$ alkyl;

$CR^2R^3$ may be the radical of a naturally occurring amino acid;

$R^4$ is H, halogen, —$NO_2$, —CN, —$OR^2$, —$SR^2$, $C_1$-$C_8$ alkyl, or —(C=O)$R^2$;

$R^5$ is

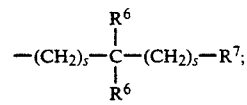

$R^6$ is H or $C_1$-$C_4$ alkyl;

$R^7$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
(B) the radical W—$R^8$;

$R^8$ contains up to 21 carbon atoms and is (1) a hydrocarbon radical or (2) an acyl radical of an organic acyclic or monocyclic carboxylic acid containing not more than 1 heteroatom in the ring;

$R^9$ is —$OR^{10}$, —$SR^{10}$, or $NR^{10}R^{10}$;

$R^{10}$ is H, $C_1$-$C_6$ alkyl, —(C=O)$R^{11}$, unsubstituted phenyl, unsubstituted benzyl, or two $R^{10}$ groups joined to the same N may form a ring of 5 or 6 members containing up to two heteratoms chosen from O, S or N;

$R^{11}$ is H, $C_1$-$C_8$ alkyl, $C_2$-$C_8$ alkenyl, $C_2$-$C_8$ alkynyl, —$CF_3$, or unsubstituted phenyl, benzyl, or phenethyl;

$R^{12}$ is $R^2$ or halogen;

m and m' are independently 0-8;

n and n' are independently 0 or 1;
p and p' are independently 0–8;
m+n+p is 1–10;
m' +n' +p' is 1–10; $Q^1$ and $Q^2$ are independently —$COOR^2$, tetrazole, —$COOR^5$, —$CONHS(O)_2R^{11}$, —CN, —$CONR^{10}R^{10}$, —CHO, —$CH_2OH$, —$COCH_2OH$, —$NHS(O)_2R^{11}$; or if $Q^1$ or $Q^2$ is COOH and $R^3$ is —OH, —SH, or —$NHR^2$ then $Q^1$ or $Q^2$ and $R^3$ and the carbons through which they are attached may form a heterocyclic ring with loss of water;
W is O, S, or NH;
$X^1$ is O, S, —S(O)—, —$S(O)_2$—, —$NR^2$, or —$CR^2R^2$—;
$X^2$ and $X^3$ are independently S, S(O), or $S(O)_2$;
Y is —$CR^2=CR^2$—, —C≡C—, —$CR^2R^2$—$X^1$—, —$X^1$—$CR^2R^2$—, —$CR^2R^2$—$X^1$—$CR^2R^2$—,

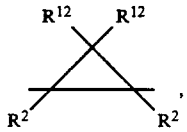

C=O,

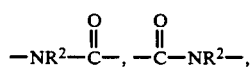

O, S, or —$NR^2$;
$Z^1$ and $Z^2$ are independently —$CONR^2$—;
and the pharmaceutically acceptable salts thereof.

Alkyl, alkenyl, and alkynyl are intended to include linear, branched, and cyclic structures.

Alkyl groups include methyl, ethyl, propyl, isopropyl, butyl sec- and tert-butyl, pentyl, hexyl, heptyl, cyclopropyl, cyclobutyl, cyclopentyl, cyclohexyl, cycloheptyl, norbornyl and the like.

Alkenyl groups include vinyl, allyl, isopropenyl, pentenyl, hexenyl, heptenyl, cyclopropenyl, cyclobutenyl, cyclopentenyl, cyclohexenyl, cycloheptenyl, 1-propenyl, 2-butenyl, 2-methyl-2-butenyl, norbornenyl, and the like.

Substituted phenyl, benzyl, and phenethyl include 1 or 2 substituents on the benzene ring selected from $C_1-C_6$ alkyl, $R^9$, $NO_2$, $SCF_3$, halogen, —$COR^6$, —$COR^9$, CN, and $CF_3$.

Halogen includes F, Cl, Br and I.

The prodrug esters of Q (i.e., when Q=—$COOR^5$) are intended to include the esters such as are described by Saari et al., J. Med Chem., 21, No. 8, 746–753 (1978).

When Q and $R^3$ and the carbons through which they are attached form a ring, the rings thus formed include lactones, lactams, and thiolactones.

It is intended that the definitions of any substituent (e.g., $R^1$, $R^2$, m, Q, X, etc.) in a particular molecule be independent of its definitions elsewhere in the molecule. Thus, —$NR^2R^2$ represents —NHH, —$NHCH_3$, —$NHC_6H_5$, etc.

The heterocycles formed when two $R^{10}$ groups join through N include pyrrolidine, piperidine, morpholine, thiamorpholine, piperazine, and n-methylpiperazine.

The naturally occurring amino acids, the radicals of which may be $CR^2R^3$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Examples of Z—$CR^2R^3$—Q containing a naturally occurring amino acid radical include:

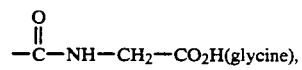

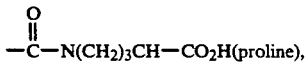

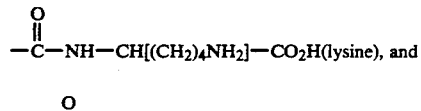

Some of the compounds described herein contain one or more centers of asymmetry and may thus give rise to diastereoisomers and optical isomers The present invention is meant to comprehend such possible diastereoisomers as well as their racemic and resolved, optically active forms Some of the compounds described herein contain olefinic double bonds, and unless specified otherwise, are meant to include both E and Z geometric isomers.

Another embodiment of the compounds of Formula I are the aryldithiaalkanedioic acids of Formula C:

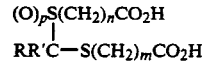            C

The present invention relates to methods for the preparation of compounds having activity as leukotriene and SRS-A antagonists or inhibitors.

Because of their activity as leukotriene antagonists or inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

SCHEME I

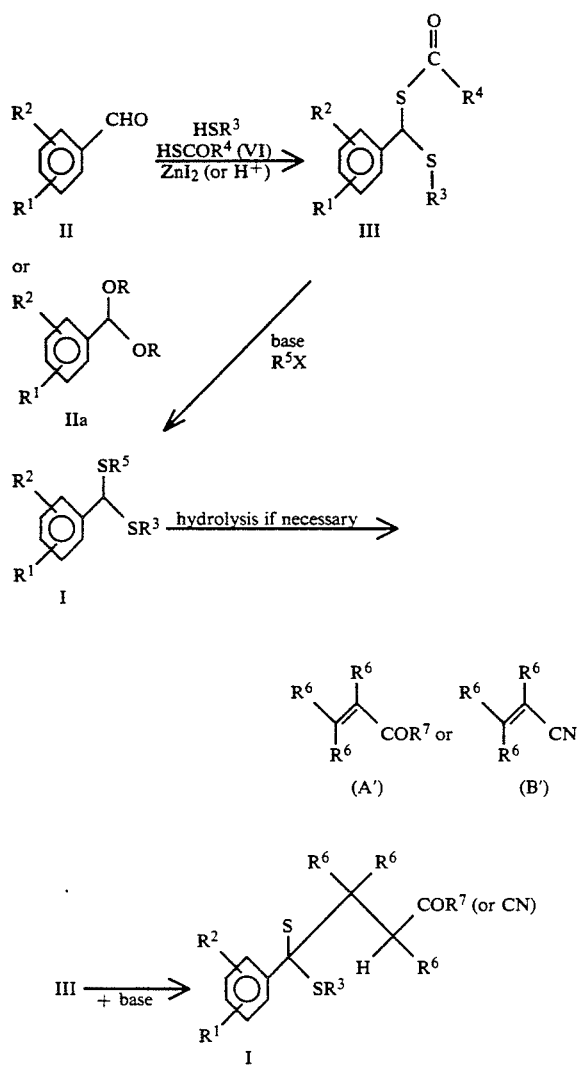

General Scheme I

An arylaldehyde of general formula II, or arylacetal of general formula IIa (where $R=C_1-C_5$ alkyl) is reacted with equal equivalents, and preferably 1.1 equivalent each of a thiol ($HSR^3$) and a thioacyl compound

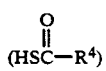

in the presence of catalytic amounts of a Lewis acid such as zinc iodide or a protic acid such as p-toluenesulphonic acid in inert solvent such as toluene or dichloroethane at room temperature or with mild heating to provide the mixed thioacyl-thioalkylacetal of general formula III. The compound III is purified by chromatography or crystallization techniques and then treated with a base such as sodium carbonate, sodium hydroxide or sodium methoxide in a solvent such as methanol or the like either in the presence of or followed by the addition of a reactive electrophile such as $R^5X$, where X is a good leaving group such as halogen or methanesulfonate or the like, to provide the asymetric thioacetal of general formula I. An $\alpha, \beta$-unsaturated carbonyl or nitrile compound of formula A' or B' may also be used as an electrophile in place of $R^5X$ to produce I.

$R^1$ and $R^2$ can be chosen from a wide variety of substituents such as $-CR^6=O$, $-COR^7$, $-C\equiv N$, $CH_2-O-R^8$, $-CH_2-O-(2\text{-quinolinyl})$ $-CH=CH-(2\text{-quinolinyl})$, $-C\equiv C-(2\text{-quinolinyl})$, $-O-CH_2-(2\text{-quinolinyl})$ (or substituted quinolinyl*), straight chain and branched alkyl of $C_1-C_{20}$, alkylaryl where alkyl is of $C_1-C_{20}$ and aryl is substituted with $R^9$ or two groups (where $R^9=H$, lower alkyl, lower alkyloxy, lower alkylthio, halogen, $-CF_3$, $SCF_3$) or $R^1$ can be (3-(4-acetyl-3-hydroxy-2-propylphenoxy)propylthio- or (3-(4-acetyl-3- hydroxy-2-propylphenoxy)propylsulfonyl.

* Where 2-quinolinyl is mentioned it may be optionally substituted with groups R' such as halogen, CF3, R, SCF3, aryl, etc.

$R^3$ can be chosen from a wide variety of groups such as alkyl of $C_1-C_{20}$, substituted aryl, or arylalkyl where aryl substituents may include $R^9$ and $COR^7$, and preferably $-(CR_2^6)COR^7$ and $-(CR_2^6)_n$-tetrazole. $R^4$ is alkyl or aryl substituted with $R^9$ or alkylaryl and the like and may include

such that when the two $R^6$ groups are different from each other and from $R^9$ then this group may be chiral and serve as a chiral auxillary.

$R^5$ can be alkyl, substituted arylalkyl-, and preferably $-(CR_2^6)_n-COR^7$, or $-(CR_2^6)_n$-tetrazole.

$R^6$ can be hydrogen, aryl, lower alkyl, hydrogen, or $-CF_3$.

$R^7$ can be hydroxy, alkyloxy, aryloxy, $N(R^6)_2$, or prodrug esters $R^8$ can be hydrogen, $-Si(R^6)_3$, aryl, substituted aryl,

and the like, as is compatible with the reagents employed.

n can be 1 to 6.

Generally, $R^1$, $R^2$, $HSR^3$, and the electrophile are defined so as to produce compounds of Formula I.

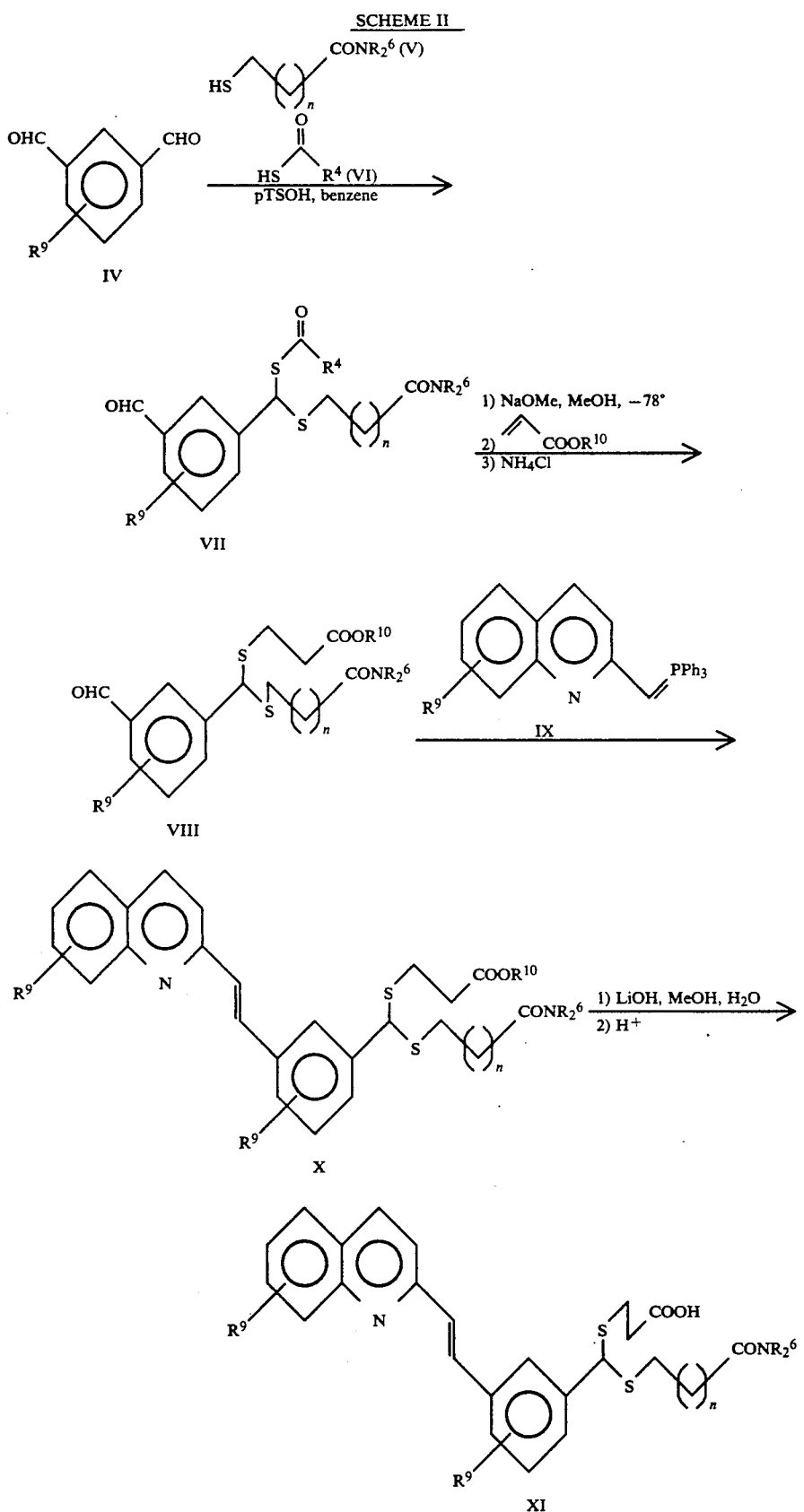
SCHEME II
A dialdehyde of general structure IV is reacted with 1.1 equivalents of each V and VI in a solvent such as benzene with an acid such as P-toluenesulphonic acid to give the compound of general formula VII which is purified by chromatography. The purified VII is reacted in ethanol or methanol-THF preferably at low temperature but also up to room temperature with a base such as NaOMe (or NaOH or $Na_2CO_3$) followed by reaction with an acrylic ester or acid $CR_2^6=CR^6-COOR^{10}$, in which $R^{10}$ is lower alkyl or $-Si(alkyl)_3$ to give the asymmetric thioacetal VIII. VIII is reacted in a solvent such as THF with an ylid such as IX to give X which is hydrolyzed with a base such as LiOH to give the leukotriene antagonist of general structure XI.

5,136,034
SCHEME III
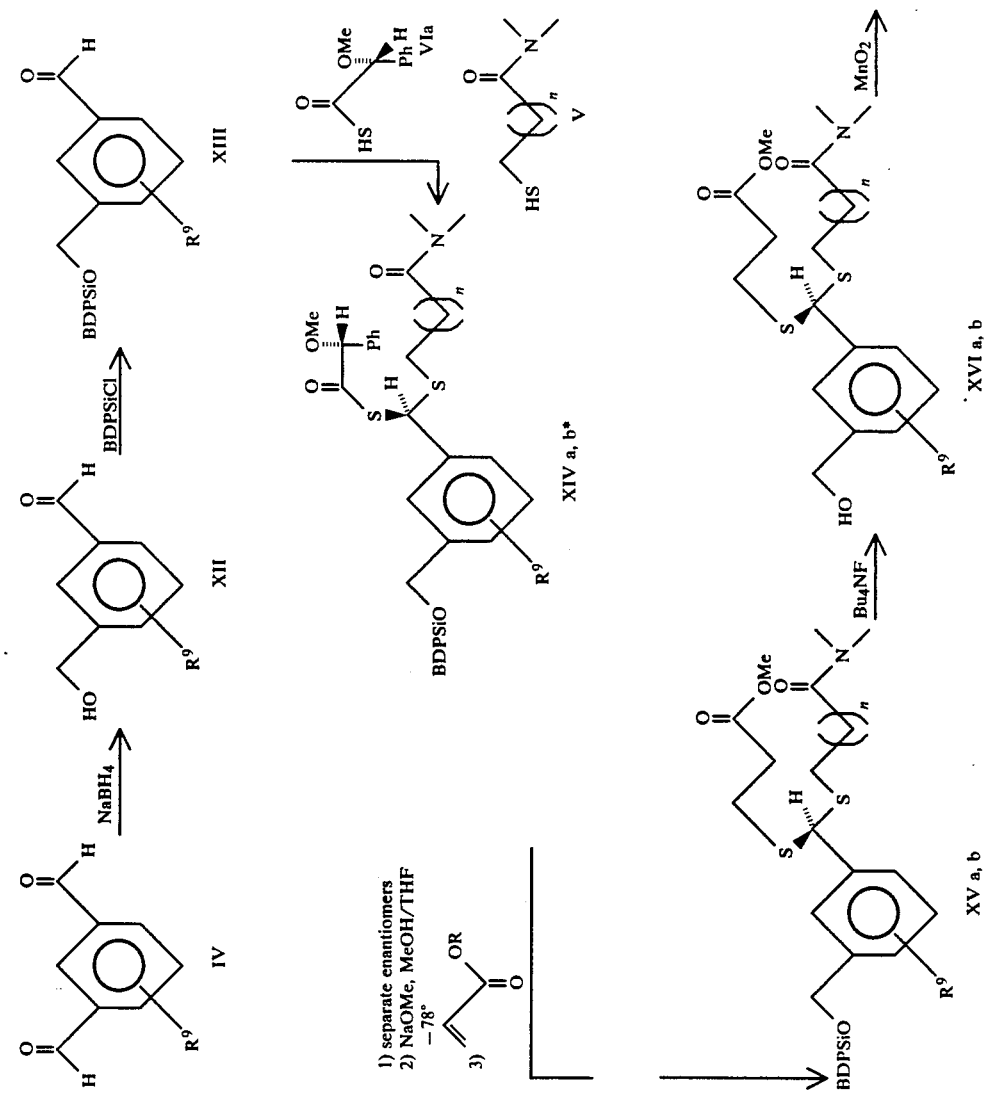

SCHEME III
-continued
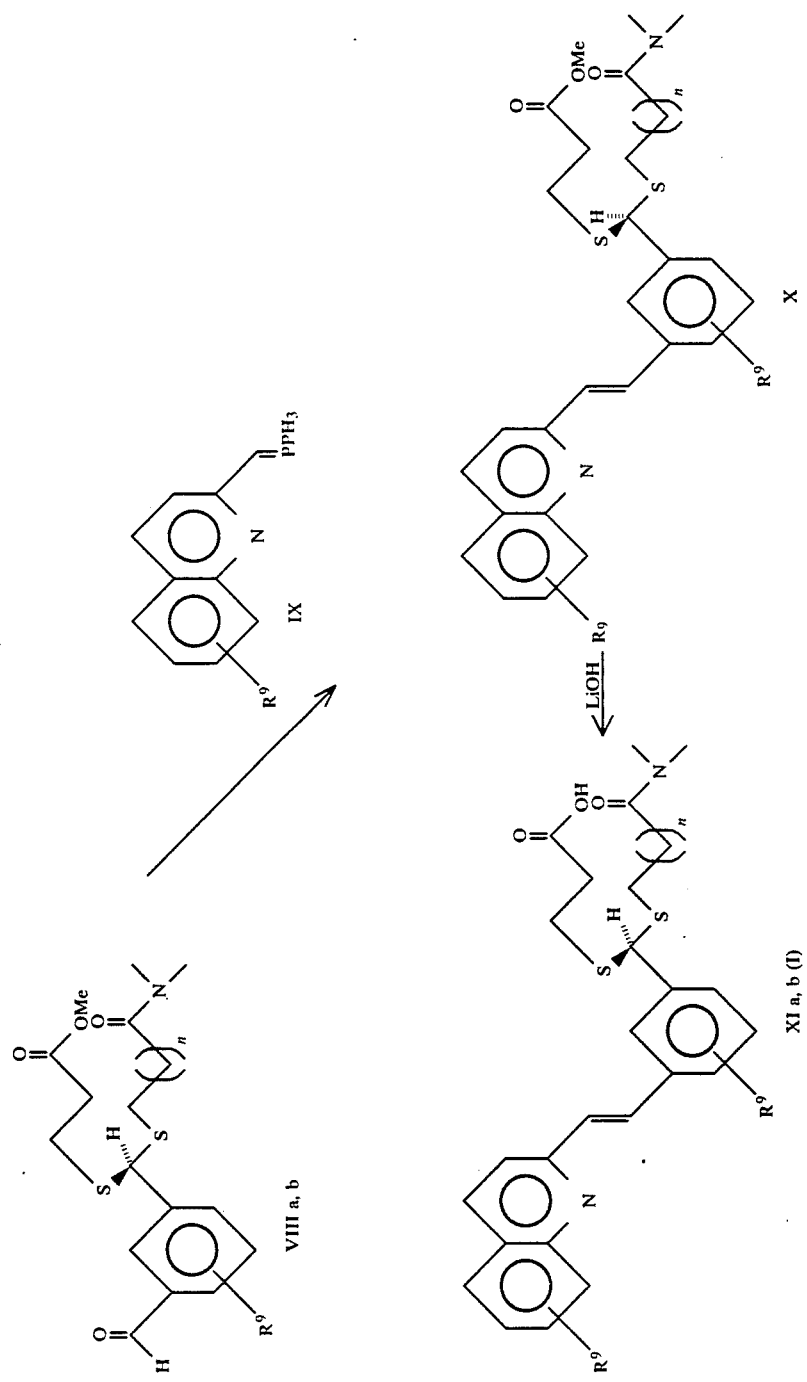

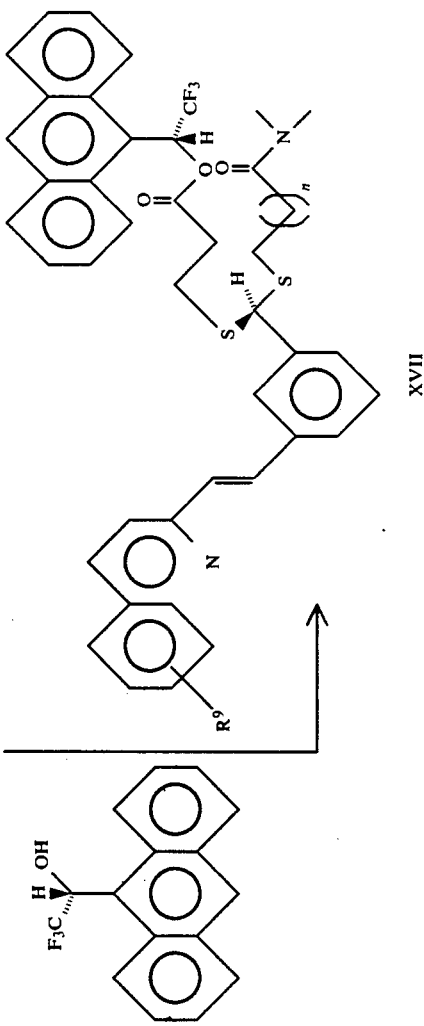
*Only one chiral isomer is depicted.
BDPSiCl = t-butyldiphenyl silyl chloride

SCHEME III

If the thioacyl reagent VI contains an adjacent chiral center such as in the case of R-(—)-α-methoxy-α-phenylthioacetic acid (prepared as described in Scheme V), then the thioacylthioalkyl acetal XIV can be separated by chromatographic techniques to give the diasteromeric XIVa and XIVb The pure XIVa (or b) can then be reacted as previously described but ensuring that the reaction never rises above −40° C., to give after quenching with NH₄Cl at −78° C., the chiral thioacetal XVa (or XVb from XIVb). Removal of the protecting silyl group wit Bu₄NF and oxidation of the alcohol (XVI) with manganese dioxide gives the aldehyde VIIIa (or VIIIb) which is reacted with the ylid,IX to give after ester hydrolysis the chiral leukotriene antagonist XIa (or its enantiomer XIb). The compound XI can be converted to a chiral ester such as XVII in order to assess chiral purity either by NMR or HPLC analysis of the resulting diastereomers.

SCHEME IV

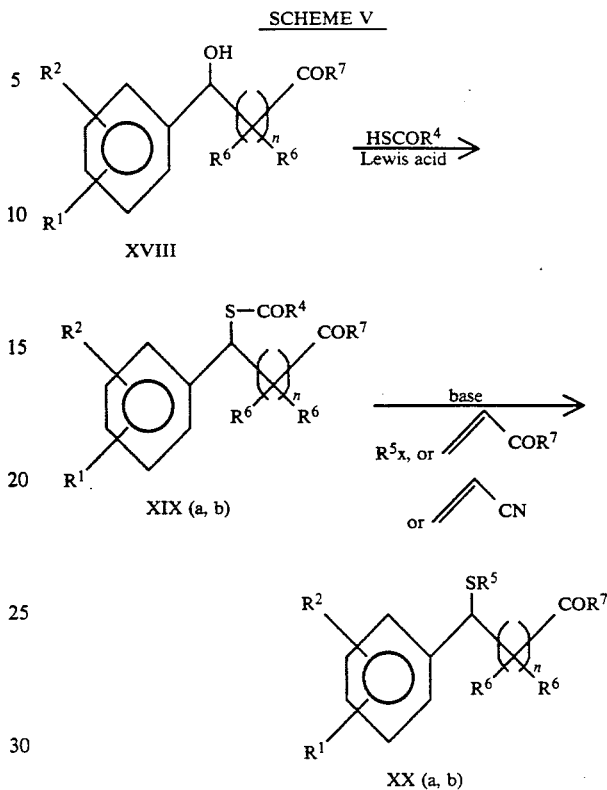

SCHEME IV

The preferred chiral thioacid can be prepared by standard methods from the corresponding (in this case commercially available) chiral acid as shown in Scheme IV.

The 2-dimethylcarbamoylethanethiol can be prepared from dimethylacrylamide and thioacetic acid followed by base hydrolysis as shown in Scheme V.

SCHEME V

SCHEME V

A similar procedure can be applied in the synthesis of arylthioethers of general formula XX. An alcohol of general formula XVIII is reacted with a thiolacid of general formula HS—CO—R⁴ in the presence of a Lewis acid such as zinc iodide or aluminum chloride in an inert solvent such as dichloromethane or 1,2-dichloroethane to provide the thioacyl derivative XIX. When the thiolacid HSCO—R⁴ contains a chiral center (such as for VIa of Scheme III) then XIX will be a diasteromeric pair of isomers which can be normally separated by chromatographic or crystallization techniques to provide the pure diasteromers XIXa and XIXb. The acylthio derivative XIX is reacted with a base such as NaCO₃, NaOH, or NaOMe and then with an electrophile such as R⁵X or CR₂⁶=CR⁶—COR⁷ or CR₂⁶=CR⁶—CN followed by quenching with NH₄Cl or water and isolation of the product XX. When XX contains ester groups or protecting groups these groupings can then be removed by standard techniques (or further elaborations made as required) to provide the leukotriene antagonists. When this procedure is applied to the diastereomers (XIXa and XIXb) then the pure enantiomers of XX (XXa and XXb) are obtained. In this case NaOMe is the base of choice, in a solvent such as THF-methanol, and the temperature of the final alkylation step should be maintained at less than −40° C. and preferably at −78° C.

SCHEME VI

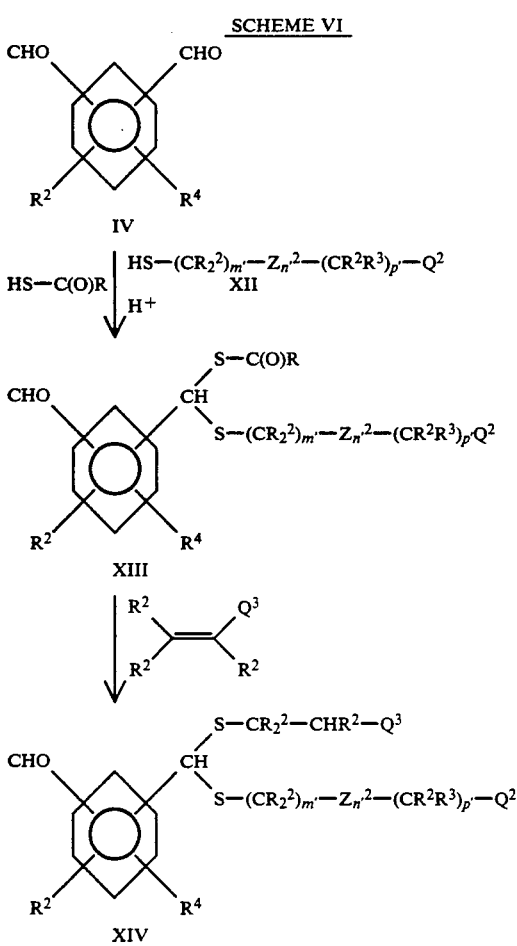

SCHEME VI

An alternate preparation of compounds of type XIV, a subtype of I, is as follows A dialdehyde of structure IV is reacted with one equivalent of the appropriate thiol XII and one equivalent of thiol acid, RC(O)SH, in a solvent such as benzene with an acid such as p-toluenesulfonic acid to give the compound of general structure XIII which is purified by chromatography. The purified XIII is reacted in methanol or ethanol preferably at low temperature but also up to room temperature with a base such as NaOMe (or NaOH or Na$_2$CO$_3$) followed by a Michael acceptor olefin to give asymmetric thioacetal XIV.

In Scheme VI, Q$^3$ is —COOR$^2$, —COOR$^5$, —CN, or —CONR$^{10}$R$^{10}$ or CHO and R is C$_1$-C$_{12}$ alkyl, an optically active carboxylic acid such as α-methoxy phenylacetic acid, abietic acid, camphoric acid, cis-2-benzamidocyclohexane carboxylic acid, diacetyl tartaric anhydride, α-methoxy-α-trifluoromethylphenylacetic acid, menthyloxyacetic acid, 2-methylbutyric acid, 2-phenylbutyric acid, 2-phenylpropionic acid or pyroglutamic acid.

The invention is further defined by reference to the following examples, which are intended to be illustrative and not limiting.

All temperatures are in degrees Celsius.

EXAMPLE 1

(+)-5-(3-(2-(7-CHLOROQUINOLIN-2-YL)ETHENYL)PHENYL)-8-DIMETHYLCARBAMYL-4,6-DITHIAOCTANOIC ACID

Step 1: Preparation of 3-hydroxymethylbenzaldehyde

To a solution of isophtalaldehyde (8 g) in ethanol (80 mL) at room temperature was added NaBH portion wise, until about 50% reaction by TLC. The reaction mixture was quenched with 25% ammonium acetate, extracted with ethyl acetate, which was washed with brine (2x), dried over sodium sulfate, filtered and evaporated to dryness. Purification of the residue by flash chromatography using 50% ether in hexane afforded the pure title compound.

$^1$H NMR (CDCl$_3$) δ 2.45 (s, 1H, OH), 4.78 (s, 2H, CH$_2$OH), 7.50–7.90 (m, 4H, Ar), 10.05 (s, 1H, CHO).

Step 2: Preparation of 3-t-butyldiphenylsilyloxymethylbenzaldehyde

To a solution of 3-hydroxymethylbenzaldehyde (step 1) (3 g) in methylene chloride (15 mL) and triethylamine (4.1 mL) was slowly added t-butylchlorodiphenylsilane (8 mL). Finally, a few mgs of 4-pyrrolidinopyridine was added as a catalyst. The reaction mixture was stirred overnight at room temperature The solution was quenched with 25% ammonium acetate and extracted with ethyl acetate, which was washed with brine (2x), dried over sodium sulfate, filtered and evaporated to dryness. Purification by flash chromatography, using 4% ethyl acetate in hexane afforded the title compound.

$^1$H NMR (CDCl$_3$) δ 1.13 (s, 9H, t-Bu), 4.82 (s, 2H, CH$_2$O), 7.25–7.85 (m, 14H, Ar), 10.05 (s, 1H, CHO).

Step 3: Preparation of (R)-(+)-α-methoxybenzenethanethioic acid

To (R)-(—)-α-methoxyphenylacetic acid (2 g) in benzene (20 mL) at —10° C. was slowly added oxalyl chloride (1.15 mL) and 1 drop of DMF. The solution was slowly warmed to room temperature and stirred for 2 hrs. The solvent was evaporated and the oily residue was coevaporated with toluene (3x). This acid chloride was used as such.

I.R. (neat) 1790 cm$^{-1}$ (C=O).

To ethanol (20 mL) at —10° C., anhydrous NaSH (1.34 g, 2 eq) was added. Then, the acid chloride in THF (8 mL) was slowly added. The reaction mixture was stirred for 20 min at —10° C. The mixture was acidified with 6N HCl, extracted with EtOAc, washed with brine (2x), dried Na filtered and evaporated to dryness to afford (R)-(+)-α-methoxybenzenethanethioic acid.

[α $_D^{25}$ 32.7 (C=3.1, acetone). IR (neat) 2550 (SH) and 1700 cm$^{-1}$ (C=O)

Step 4: Preparation of 3-mercapto—N,N-dimethylpropanamide

To N,N-dimethylacrylamide (19.8 g, 0.2 mol) at 0° C., was slowly added thioacetic acid (15.22 g, 0.2 mol). The ice-bath was then removed and the reaction mixture stirred at room temperature for 15 min. On distillation (b.p. 96-98° /0.06 Tor) a reddish oil was obtained To this oil (5.66 g, 32.34 mmol.) in methanol (20 mL) at 0° C. was added potassium t-butoxide (3.622 g, 1 eq) in 3 portions The mixture was stirred at room temperature for 1.5 hr. The reaction mixture was poured over 25% ammonium acetate and methylene chloride. 2N HCl was added to bring the pH to 7.0–7.5. After 2 more extractions with methylene chloride, the organic layers were combined, dried over sodium sulfate, filtered, and evaporated to dryness to afford 3-mercapto—N,N-dimethylpropanamide as a pale orange oil.

Step 5: Preparation of (−)-methyl 5-(3-(t-butyldiphenylsilyloxymethyl)phenyl)-8-dimethylcarbamyl-4,6-dithiaoctanoate To a solution of 3-t-butyldiphenylsilyloxymethylbenzaldehyde (step 2) (8.98 g, 24 mmol.) in benzene (90 mL) was added 3-mercapto—N,N-dimethylpropanamide (step 4) (3.5 g, 26 mmol.), (R)-(+)-α-methoxybenzenethanethioic acid (step 3) (4.76 g, 26 mmol.) and p-toluenesulfonic acid (2.26 g, 13 mmol.). The solution was refluxed for 3.5 hrs with a DeanStark apparatus filled with activated 3A molecular sieve. The solution was cooled to room temperature, quenched with 25% ammonium acetate, and extracted with EtOAc, which was washed with brine (3x), dried over sodium sulfate, filtered and evaporated to dryness. The two diastereomers were separated by flash chromatography using 40% of ethyl acetate in hexane.

Less polar compound:
$^1$H NMR (CDCl$_3$) δ 1.12 (s, 9H, t-Bu), 2.45 (t, 2H, J=7 Hz, CH$_2$), 2.78 (t, 2H, J=7 Hz, CH$_2$), 2.82 and 2.88 (2s, 6H, N(CH$_3$)$_2$), 3.42 (s, 3H, OCH$_3$), 4.70 (s, 1H, CH), 4.74 (s, 2H, CH$_2$O), 5.61 (s, 1H, CH), 7.26-7.71 (m, 19H, Ar).

More polar compound:
$^1$H NMR (CDCl$_3$) δ 1.10 (s, 9H, t-Bu), 3.59 (t, 2H, J=7 Hz, CH$_2$), 3.85 (t, 2H, J=7 Hz, CH$_2$), 3.95 and 3.96 (2s, 6H, N(CH$_3$)$_2$), 3.48 (s, 3H, OCH$_3$), 4.72 (s, 2H, CH$_2$O), 4.78 (s, 1H, CH), 5.64 (s, 1H, CH), 7.26-7.85 (m, 19H, Ar).

A solution of the less polar compound (2.6 g, 3.87 mmol.) in THF (40 mL) was cooled to −78° C. A solution of sodium methoxide (1M) in methanol (3.47 mL, 0.9 eq) was added. After stirring for 10 min (−78° C.), methyl acrylate (0.52 mL, 1.5 eq) was added and the solution was stirred for 2 hrs at −78° C. The reaction mixture was quenched at low temperature with a saturated solution of ammonium chloride, and extracted with EtOAc, which was washed with brine (3×), dried over sodium sulfate, filtered and evaporated to dryness. Purification by flash chromatography using 40% ethyl acetate in hexane afforded the title compound.

[α]$_D^{25}$ −1.62 (C=1.22, acetone).

$^1$H NMR (CDCl$_3$) δ 1.12 (s, 9H, t-Bu), 2.50–2.90 (m, 8H, 4(CH$_2$)), 2.91 and 2.92 (2d, 6H, N(CH$_3$)$_2$), 3.68 (s, 1H, OCH$_3$), 4.77 (s, 2H, CH$_2$O), 5.00 (s, 1H, CH), 7.27–7.72 (m, 14H, Ar).

Step 6: Preparation of (−)-meth-yl 5-(3-(hydroxymethyl)phenyl)-8-dimethylcarbamyl-4,6-dithiaoctanoate To a solution of (-)-meth-yl 5-(3-(t-butyldiphenylsilyloxymethyl)phenyl)-8-dimethylcarbamyl-4,6-dithiaoctanoate (step 5) (1.377 g, 2.26 mM) in THF (25 mL) at room temperature was slowly added tetra-n-butylammonium fluoride (1M) in THF (2.34 mL). The solution was stirred 2 hrs at room temperature Ethyl acetate was added to the reaction mixture, and the organic layer it was washed with brine (3x), dried over sodium sulfate, filtered and evaporated to dryness. Purification by flash chromatography using 40% acetone in hexane afforded the title compound.

[α]$_D^{25}$ −4.2 (C=2.04, acetone).

$^1$H NMR (CDCl$_3$) δ 2.50–2.91 (m, 8H, 4(CH$_2$)), 2.94 and 2.96 (2s, 6H, N(CH$_3$)$_2$), 3.70 (s, 3H, OCH$_3$), 4.69 (s, 2H, CH$_2$OH), 5.05 (s, 1H, CH), 7.26–7.49 (m, 4H, Ar).

Step 7: Preparation of (−)-meth-yl 5-(3-formylphenyl)-8-dimethylcarbamyl-4,6-dithiaoctanoate To a solution of (−)-methyl 5-(3-(hydroxymethyl)phenyl)-8-dimethylcarbamyl-4,6-dithiaoctanoate (step 6) (679 mg) in ethyl acetate (30 mL) was added activated manganese oxide (1.3 g). The suspension was stirred overnight at room temperature. The suspension was filtered on a pad of silica gel and washed with EtOAc. The solvent was evaporated, affording the title compound.

[α]$_D^{25}$ 6.9 (C=1.73, acetone).

(CDCl$_3$) δ 2.56–2.94 (m, 8H, 4(CH$_2$)), 2.95 and 2.97 (2s, 6H, N(CH , 3.70 (s, 3H, OCH$_3$), 5.14 (s, 1H, CH), 7.52, 7.80 and 7.98 (t, t and s, 4H, Ar), 10.03 (s, 1H, CHO).

Step 8: Preparation of (−)-methyl 5-(3-(2-(7-chloroquinoline--yl)ethenyl)phenyl)-8-dimethylcarbamyl-4,6-dithiaoctanoate To a suspension of 7-chloroquinolin-2-ylmethyltriphenylphosphonium bromide (809 mg, 1.56 mmol.) (Example 4, Step 2) in THF (15 mL) at −78° C., was added a solution of n-BuLi (1.6M) in hexane (0.89 mL, 1.43 mM). The mixture was stirred for 0.5 hrs at −78° C. Then, (−)-methyl 5-(3-formylphenyl)-8-dimethylcarbamyl-4,6-dithiaoctanoate (step 7) (480 mg, 1.3 mmol.) in THF (4 mL) was slowly added. The mixture was stirred for 0.5 hr at −78° C. and then warmed up to room temperature and stirred for an additional 2 hrs. A solution of 25% ammonium acetate was added, the mixture was extracted with ethyl acetate, and the extracts were washed with brine (3×), dried over sodium sulfate, filtered and evaporated to dryness. Purification by flash chromatography afforded the title compound.

[α]$_D^{25}$ 4.2 (C=1.28, acetone).

$^1$H NMR 2.54–2.93 (m, 8H, 4(CH$_2$)), 2.94 (s, 6H, N(CH$_3$)$_2$), 3.70 (s, 1H, OCH$_3$), 5.08 (s, 1H, CH), 7.34–8.14 (m, 11H, Ar).

Step 9:

To a solution of (−)-methyl 5-(3-(2(7-chloro-quinolin-2-yl)ethenyl)phenyl)-8-dimethyl-carbamyl-4,6-dithiaoctanoate (step 8)(640 mg, 1.21 mmol.) in peroxide-free 1,2-dimethoxyethane (15 mL) and water (1.5 mL) was added LiOH (1M, 1.8 mL, 1.8 mmol.). The solution was stirred for 3 hrs at room temperature water was added and the mixture was washed with EtOAc. The aqueous layer was acidified with 1N HCl, extracted with EtOAc, the extracts were washed with brine (2×), dried over Na$_2$SO$_4$, filtered and evaporated to dryness The oily residue was coevaporated 3 or 4 times with EtOAc and finally was allowed to crystallize in this solvent overnight at 0° C. Filtration afforded the title compound.

[α]$_D^{25}$ +9.1 (C=0.88, 1% NaHCO$_3$).

$^1$NMR 2.70–3.19 (m, 8H, 4(CH )), 3.00 and 3.02 (2s, 6H, N(CH 2), 5.15 (s, 1H, CH), 7.34–8.14 (m, 11H, Ar).

EXAMPLE 2

(−)-5-(3-(2-(7-Chloroquinolin-2-yl)ethenyl)phenyl)-8-dimethylcarbamyl-4,6-dithiaoctanoic acid Step 1: Preparation of (+)-methyl 5-(3-(t-butyldiphenylsilyloxymethyl)phenyl)-8-dimethylcarbamyl-4,6-dithiaoctanoate To a solution of 3-t-butyldiphenylsilyloxymethylbenzaldehyde (Example 27, step 2) (8.98 g, 24 mmol.) in benzene (90 mL) was added 3-mercapto—N,N-dimethylpropanamide (Example 27, step 40 (3.5 g, 26 mmol.), (R)-(+)-α-methoxybenzenethanethioic acid (4.76 g, 26 mmol.) and p-toluenesulfonic acid (2.26 g, 13 mmol.). The solution was refluxed for 3.5 hrs with a Dean—Stark apparatus filled with activated 3A molecular sieve. The solution was cooled to room temperature, quenched with 25% ammonium acetate, and extracted with EtOAc, which was washed with brine (3×), dried over sodium sulfate, filtered and evaporated to dryness. The two diastereomers were separated by flash chromatography using 40% of ethyl acetate in hexane.

Less polar compound:

$^1$H NMR (CDCl$_3$) δ 1.12 (s, 9H, t-Bu), 2.45 (t, 2H, J=7 Hz, CH$_2$), 2.78 (t, 2H, J=7 Hz, CH ), 2.82 and 2.88 (2s, 6H, N(CH$_3$)$_2$), 3.42 (s, 3H, OCH$_3$), 4.70 (s, 1H, CH) 4.74 (s, 2H, CHO$_2$), 5.61 (s, 1H, CH), 7.26–7.71 (m, 19H, Ar).

More polar compound:

$^1$H NMR (CDCl$_3$)δ 1.10 (s, 9H, t-Bu), 3.59 (t, 2H, J=7 Hz, CH$_2$), 3.85 (t, 2H, J=7 Hz, CH$_2$), 3.95 and 3.96 (2s, 6H, N(CH$_3$)$_2$), 3.48 (s, 3H, OCH ), 4.72 (s, 2H, CHO$_2$), 4.78 (s, 1H, CH), 5.64 (s, 1H, CH), 7.26–7.85 (m, 19H, Ar).

A solution of the more polar compound (2.6 g, 3.87 mmol.) in THF (40 mL) was cooled to −78° C. A solution of sodium methoxide 1M in methanol (3.47 mL, 0.9 eq) was added. After stirring for 10 min (−78° C.), methyl acrylate (0.52 mL, 1.5 eq) was added and the solution was stirred for 2 hrs at −78° C. The reaction mixture was quenched at low temperature with a saturated solution of ammonium chloride, and extracted with EtOAc, which was washed with brine (3×), dried over sodium sulfate, filtered and evaporated to dryness. Purification by flash chromatography using 40% ethyl acetate in hexane afforded the title compound.

$[α]_D^{25}$ +2.05 (C=1.84, acetone).

$^1$H (CDCl$_3$) δ 1.12 (s, 9H, t-Bu), 2.50–2.90 (m, 8H, 4(CH$_2$)), 2.91 and 2.92 (2d, 6H, N(CH , 3.68 (s, 1H, OCH$_3$), 4.77 (s, 2H, CH$_2$O), 5.00 (s, 1H, CH), 7.27–7.72 (m, 14H, Ar)

Step 2: Preparation of (+)-methyl 5-(3-(hydroxymethyl)phenyl)-8-dimethylcarbamyl-4,6-dithiaoctanoate To a solution of (+)-methyl 5-(3-(t-butyldiphenylsilyloxymethyl)phenyl)-8-dimethylcarbamyl-4,6-dithiaoctanoate (step 1) (1.377 g, 2.26 mmol.) in THF (25 mL) at room temperature was slowly added tetra-n-butylammonium fluoride 1M in THF (2.34 mL). The solution was stirred 2 hrs at room temperature Ethyl acetate was added to the reaction mixture, it was washed with brine (3×), dried over sodium sulfate, filtered and evaporated to dryness. Purification by flash chromatography using 40% acetone in hexane afforded the title compound.

$^1$H NMR (CDCl$_3$) δ 2.50–2.91 (m, 8H, 4(CH$_2$)), 2.94 and 2.96 (2s, 6H, N(CH$_3$)$_2$), 3.70 (s, 3H, OCH$_3$), 4.69 (s, 2H, CH$_2$OH), 5.05 (s, 1H, CH), 7.26–7.49 (m, 4H, Ar).

Step 3: Preparation of (+)-methyl 5-(3-formylphenyl)-8-dimethylcarbamyl-4,6-dithiaoctanoate To a solution of (+)-methyl 5-(3-(hydroxymethyl)phenyl)-8-dimethylcarbamyl-4,6-dithiaoctanoate (step 2) (679 mg) in ethyl acetate (30 mL) was added activated manganese oxide (1.3 g). The suspension was stirred overnight at room temperature. The suspension was filtered on a pad of silica gel and washed with EtOAc. The solvent was evaporated, affording the title compound.

$[α]_D^{25}$ +6.7 (C=1.38, acetone)

$^1$H NMR (CDCl$_3$)δ 2.56–2.94 (m, 8H, 4(CH$_2$)), 2.95 and 2.97 (2s, 6H, N(CH$_3$)$_2$), 3.70 (s, 3H, OCH$_3$), 5.14 (s, 1H, CH), 7 52, 7.80 and 7.98 (t, t and s, 4H, Ar), 10.03 (s, 1H, CHO).

Step 4: Preparation of (+)-methyl 5-(3-(2-(7-chloroquinoline-2-yl)ethenyl)phenyl)-8-dimethylcarbamyl-4,6-dithiaoctanoate To a suspension of 7-chloroquinolin-2-ylmethyltriphenylphosphonium bromide (Example 4, Step 2) (809 mg, 1.56 mmol.) in THF (15 mL) at −78° C., was added a solution of n-Buli (1.6 M) in hexane (0.89 mL, 1.43 mmol.). The mixture was stirred for 0.5 hrs at -78° C. Then, (+)-methyl 5-(3-formylphenyl)-8-dimethylcarbamyl-4,6-dithiaoctanoate (step 3) (480 mg, 1.3 mmol.) in THF (4 mL) was slowly added. The mixture was stirred for 0.5 hr at −78° C. and then warmed up to room temperature and stirred for an additional 2 hrs. A solution of 25% ammonium acetate was added, the mixture was extracted with ethyl acetate, and the extracts were washed with brine (3×), dried over sodium sulfate, filtered and evaporated to dryness. Purification by flash chromatography afforded the title compound.

$[α]_D^{25}$ +3.5 (C=1.74, acetone).

$^1$H NMR 2.54–2.93 (m, 8H, 4(CH$_2$)), 2.94 (s, 6H, N(CH$_3$)$_2$), 3.70 (s, 1H, OCH$_3$), 5.08 (s, 1H, CH), 7.34–8.14 (m, 11H, Ar).

Step 5:

To a solution of (+)-methyl 5-(3-(2(7-chloroquinolin-2-yl)ethenyl)phenyl)-8-dimethylcarbamyl-4,6-dithiaoctanoate (step 4) (640 mg, 1.21 mmol.) in peroxide free 1,2-dimethoxyethane (15 mL) and water (1.5 mL) was added LiOH (1M, 1.8 mL, 1.8 mmol.). The solution was stirred for 3 hrs at room temperature Water was added and the mixture was washed with EtOAc. The aqueous layer was acidified with 1N HCl, extracted with EtOAc, the extracts were washed with brine (2×), dried over Na$_2$SO$_4$, filtered and evaporated to dryness. The oily residue was coevaporated 3 or 4 times with EtOAc and finally was allowed to crystallize in this solvent overnight at 0° C. Filtration afforded the title compound.

$[α]_D^{25}$ −9.2 (C=0.68, 1% NaHCO$_3$).

$^1$H NMR 2.70–3.19 (m, 8H, 4(CH$_2$)), 3.00 and 3.02 (2s, 6H, N(CH$_3$)$_2$), 5.15 (s, 1H, CH), 7.34–8.14 (m, 11H, Ar).

EXAMPLE 3

Preparation of 6-oxo-2-(3-methoxyphenyl)-1,8-dithiane

Method A:

To a benzene (2 cc) solution of 3-mercaptothiopropionic acid (122 mg, 1 mm) (Satsumabayashi, S., Synthesis, 881 (1977)) and p-toluenesulfonic acid (5 mg, catalytic) was added 3-methoxybenzaldehyde (272 mg, 2 mm) and the mixture was kept at room temperature for 16 hrs, then brought to reflux for two hours.

The reaction mixture was cooled, diluted with ethylacetate and washed successively with 10% sodium bicarbonate and brine. Organic layer was dried with sodium sulphate and the solvents removed in vacuo to leave a residue which was purified by chromatography (SiO$_2$) to yield the title compound.

| $^1$H NMR/90 MHz re TMS | | | |
|---|---|---|---|
| δ (ppm) | #H | | |
| 7.2–6.6 | 4 | m | Ph |
| 5.2 | 1 | s | CH |
| 3.7 | 3 | s | CH$_3$ |

-continued

| $^1$H NMR/90 MHz re TMS | | | |
|---|---|---|---|
| δ (ppm) | #H | | |
| 2.4–2.9 | 4 | m | CH$_2$—CH$_2$ |

Method B:

To a solution of 3-mercaptopropionic acid (122 mg, 1 mm) in dichloromethane (2 cc) was added 3-methoxybenzaldehyde (136 mg, 1 mm) followed by dry zinc iodide (32 mg, 0.1 mm) and the mixture was reacted at room temperature for 1 hr. An additional portion of zinc iodide (32 mg, 0.1 mm) was added and the mixture reacted for 30 minutes. It was diluted in dichloromethane and washed successively with 1N HCl, brine and the organic layer was dried with sodium sulphate.

Removal of the solvent yielded the title compound as an oil which was essentially pure.

| $^1$H NMR/90 MHz re TMS | | | |
|---|---|---|---|
| δ (ppm) | #H | | |
| 7.2–6.6 | 4 | m | Ph |
| 5.2 | 1 | s | CH |
| 3.7 | 3 | s | CH$_3$ |
| 2.4–2.9 | 4 | m | CH$_2$—CH$_2$ |

EXAMPLE 4

Preparation of 6-oxo-2-phenyl-1,3-dithiane

To a solution of benzaldehyde (1.06 g, 10 mm) and 3-mercaptothiopropionic acid (1.22 g, 10 mm) in dichloromethane (25 cc) was added dry zinc iodide (1 mm, 320 mg) and the mixture was refluxed for 3.5 hrs. It was cooled to room temperature, diluted with dichloromethane and successively washed with 1N HCl, brine and dried with sodium sulphate. Removal of the solvent yielded the essentially pure title compound.

| $^1$H NMR/90 MHz re TMS | | | |
|---|---|---|---|
| δ (ppm) | #H | | |
| 7.3–7.6 | 5 | m | Ph |
| 5.8 | 1 | s | CH |
| 2.6–3.3 | 4 | m | CH$_2$—CH$_2$ |

EXAMPLE 5

Preparation of 6-oxo-2-(4-methoxyphenyl)-1,3-dithiane

Following the procedure described in Example 4 but substituting 3-methoxybenzaldehyde for benzaldehyde, there was obtained the title compound.

| $^1$H NMR/250 MHz re TMS | | |
|---|---|---|
| δ (ppm) | #H | |
| 7.4–7.5 | 2 | d |
| 6.85–6.95 | 2 | d |
| 5.75 | 1 | s |
| 3.8 | 3 | s |
| 2.8–3.3 | 4 | m |

EXAMPLE 6

Preparation of 6-oxo-2-heptyl-1,3-dithiane

Following the procedure described for Example 4 but substituting n-octananl for benzaldehyde, there was obtained the title compound.

| $^1$H NMR/250 MHz re TMS | | |
|---|---|---|
| δ (ppm) | #H | |
| 4.6–4.7 | 1 | t |
| 3.0–3.2 | 2 | m |
| 2.75–3.0 | 4 | m |
| 1.8–2.0 | 4 | m |
| 1.2–1.6 | 9 | m |

EXAMPLE 7

Preparation of Methyl 5-(3-hydroxyphenyl)-7-oxo-4,6-dithiaoctanoate

To a dichloromethane (100 cc) solution of 3-hydroxybenzaldehyde (3.05 g, 25 mm) was added methyl 3-mercaptopropionate (3.0 g, 25 mm), thiolacetic acid (1.9 g, 25 mm), and dry zinc iodide (4.8 g, 15 mm). The mixture was reacted at room temPerature for 16 hrs and then diluted with dichloromethane, washed successively with 1N HCl, brine and dried with sodium sulphate. Removal of the solvent left a residue which was purified by chromatography (SiO$_2$) to yield the title compound.

| $^1$H NMR/90 MHz re TMS | | |
|---|---|---|
| δ (ppm) | #H | |
| 6.7–7.3 | 5 | m |
| 6.1 | 1 | s |
| 5.7 | 1 | s |
| 3.7 | 3 | s |
| 2.6–3.0 | 4 | m |
| 2.3 | 3 | s |

EXAMPLE 8

Preparation of Methyl 5-(3-methoxyphenyl)-7-oxo-4,6-dithiaoctanoate

Following the procedure described for Example 7 but substituting 3-methoxybenzaldehyde for 3-hydroxybenzaldehyde, there was obtained the title compound.

| $^1$H NMR/250 MHz re TMS | | |
|---|---|---|
| δ (ppm) | #H | |
| 6.8–7.3 | 4 | m |
| 2.7 | 1 | s |
| 3.8 | 3 | s |
| 3.7 | 3 | s |
| 2.5–3 | 4 | m |
| 2.3 | 3 | s |

EXAMPLE 9

Preparation of 5-(3-hydroxyphenyl)-7-oxo-4,6-dithiaoctanoic acid N,N-dimethylamide Following the procedure described for Example 7 but substituting N,N-dimethyl-3-mercaptopropionamide for methyl 3-mercaptopropionate, there was obtained the title compound.

| $^1$H NMR/90 MHz re TMS | | |
|---|---|---|
| δ (ppm) | #H | |
| 8.0 | 1 | bs |
| 6.7–7.3 | 4 | m |
| 5.6 | 1 | s |
| 3.0 | 6 | 2s |
| 2.5–2.9 | 4 | m |
| 2.3 | 3 | s |

EXAMPLE 10

Preparation of
5-(3-acetoxymethylphenyl)-7-oxo-4,6-dithiaoctanoic acid N,N-dimethyl Amide Following the procedure described for Example 7 but substituting 3-formalbenzylacetate for 3-hydroxybenzaldehyde and N,N-dimethyl-3-mercaptopropionamide for methyl 3-mercaptopropionate, there was obtained the title compound.

| $^1$H NMR/90 MHz re TMS | | |
|---|---|---|
| δ (ppm) | #H | |
| 7.2–7.5 | 4 | m |
| 5.75 | 1 | s |
| 5.1 | 2 | s |
| 3.0 | 6 | 2s |
| 2.5–2.8 | 4 | m |
| 2.35 | 3 | s |
| 2.1 | 3 | s |

EXAMPLE 11

Preparation of
α-Phenylthioα-Acetylthio-4-Methoxytoluene

Following the procedure described for Example 7 but substituting 4-methacybenzaldehyde for 3-hydroxybenzaldehyde and thiophenol to methyl 3-mercaptopropionate, there was obtained the title compound

| $^1$H NMR/90 MHz re TMS | | |
|---|---|---|
| δ (ppm) | #H | |
| 6.8–7.5 | 9 | m |
| 5.95 | 1 | s |
| 3.8 | 3 | s |
| 2.2 | 3 | s |

EXAMPLE 12

Preparation of α-phenylthio-α-acetylthiotoluene

Following the procedure described for Example 7 but substituting benzaldehyde for 3-hydroxy-benzaldehyde and thiophenol for methyl 3-mercaptopropionate, there was obtained the title compound.

| $^1$H NMR/90 MHz re TMS | | |
|---|---|---|
| δ (ppm) | #H | |
| 7.1–7.6 | 10 | m |
| 6.0 | 1 | s |
| 2.2 | 3 | s |

EXAMPLE 13

Preparation of Methyl
5-(4-Methoxyphenyl)-4-oxo-4,6Dithiaoctanoate

Following the procedure described for Example 7 but substituting 4-methoxybenzaldehyde for benzaldehyde, there was obtained the title compound.

| $^1$H NMR/90 MHz re TMS | | |
|---|---|---|
| δ (ppm) | #H | |
| 7.5–6.8 | 4 | m |
| 5.7 | 1 | s |
| 3.8 | 3 | s |
| 3.7 | 3 | s |
| 2.5–3.0 | 4 | m |
| 2.3 | 3 | s |

EXAMPLE 14

Preparation of Methyl
5-(3-Methoxyphenyl)-9-oxo-9-Dimethylamino-4,6-Dithianonanoate To a room temperature methanol (3 cc) solution of the compound obtained in Example 3 (75 mg, 0.31 mm) and N,N-dimethylacrylamide (62 mg, 0.62 mm) was added dry milled potassium carbonate (85 mg, mm) and the mixture was allowed to react for 1 hr. It was diluted with ethyl acetate and washed successively with 1N HCl, brine and dried with sodium sulphate. Removal of the solvent left a residue which was purified by chromatography (SiO$_2$) to yield the title compound.

| $^1$H NMR/250 MHz re TMS | | |
|---|---|---|
| δ (ppm) | #H | |
| 6.8–7.3 | 4 | m |
| 5.0 | 1 | s |
| 3.8 | 3 | s |
| 3.7 | 3 | s |
| 2.9 | 6 | s |
| 2.7–2.9 | 4 | m |
| 2.4–2.7 | 4 | m |

EXAMPLE 15

Preparation of Methyl
5-(3-hydroxyphenyl)-9-oxo-9-dimethylamino-4,6-dithianomamoate To a cooled, 0° C., solution of the compound obtained in Example 9 (200 mg, 0.63 mm), methyl acrylate (172 mg, 2 mm) in 2-butanone (4 cc) and methanol (1 cc) was added dry milled potassium carbonate (276 mg, 2 mm) and the mixture allowed to react for 16 hrs with gradual warming to room temperature.

The reaction mixture was then treated as in Example 14 to yield the title compound.

| $^1$H NMR/90 MHz re TMS | | |
|---|---|---|
| δ (ppm) | #H | |
| 6.8–7.4 | 4 | m |
| 5.0 | 1 | s |
| 3.65 | 3 | s |
| 2.2–3 | 15 | m |

EXAMPLE 16

Preparation of Methyl 5-(3-acetoxymethylphenyl)-9-oxo-9-dimethylamino-4,6-dithianonanoate To a cooled, 0° C., solution of the compound obtained in Example 10 (1.467 g, 4 mm) and methyl acrylate (1.72 g, 20 mm) in 2-butanone (20 cc) and methanol (5 cc) was added dry potassium carbonate (607 mg, 4.4 mm) and the mixture allowed to react at 0° C. for 1 hr.

The reaction mixture was then treated as in Example 14 to yield the title compound.

| $^1$H NMR/90 MHz re TMS | | |
|---|---|---|
| δ (ppm) | #H | |
| 7.2-7.6 | 4 | m |
| 5.1 | 3 | 2s |
| 3.8 | 3 | s |
| 2.8-3.0 | 14 | m |
| 2.1 | 3 | s |

What is claimed is:

1. A process which comprises:
   (1) reacting an arylaldehyde of the formula:

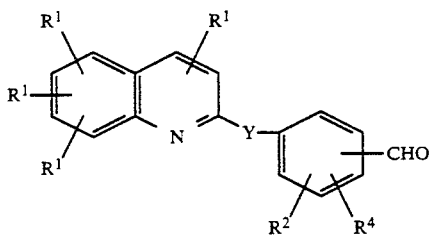

with a thiol (HSR″) and a thioacyl (HSC(O)R⁴′) in the presence of an acid catalyst to produce a thio compound of the formula:

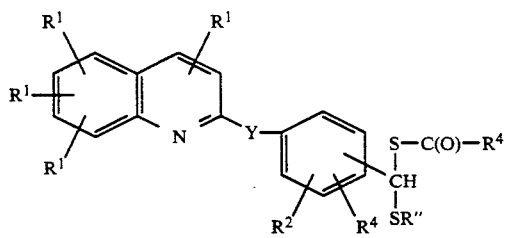

wherein:
R⁴′ is alkyl, aryl substituted with R⁹′, alkylaryl, or

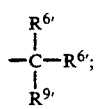

R⁶′ is H, aryl, lower alkyl, or —CF$_3$;
R⁹′ is H, loweralkyl, loweralkyloxy, lower alkylthio, halogen, —CF$_3$, or SCF$_3$; and
R″ is —(CR$_2^2$)$_m$—Z$^1_n$—(CR$^2$R$^3$)$_p$—Q$^1$ or —(CR$_2^2$)$_{m'}$—Z$^2_{n'}$—(CR$^2$R$^3$)$_{p'}$—Q$^2$;

(2) reacting said compound III with an electrophile to produce a chiral thioacetal of the formula:

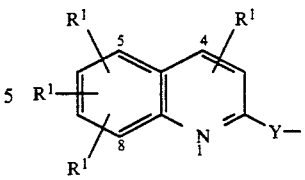

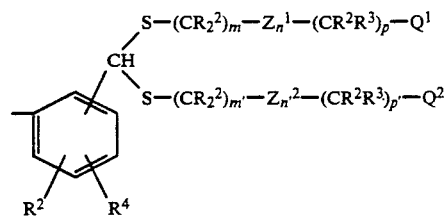

wherein:
R$^1$ is H, halogen, C$_1$-C$_8$ alkyl, C$_2$-C$_8$ alkenyl, C$_2$-C$_8$ alkynyl, —CF$_3$, —OR$^2$—SR$^2$, —S(O)R$^2$, —S(O)$_2$R$^2$, —NR$^2$R$^2$, —CHO, —COOR$^2$, —(C=O)R$^2$, —C(OH)R$^2$R$^2$, —CN, —NO$_2$, substituted or unsubstituted phenyl, substituted or unsubstituted benzyl, or substituted or unsubstituted phenethyl;
R$^2$ is H, C$_1$-C$_8$ alkyl, C$_2$-C$_8$ alkenyl, C$_2$-C$_8$ alkynyl, —CF$_3$, substituted or unsubstituted phenyl, substituted or unsubstituted benzyl, or substituted or unsubstituted phenethyl;
R$^3$ is H, halogen, —NO$_2$, —CN, —OR$^2$, —SR$^2$, NR$^2$R$^2$, or C$_1$-C$_8$ alkyl;
R$^4$ is H, halogen, —NO$_2$, —CN, —OR$^2$, —SR$^2$, NR$^2$R$^2$, C$_1$-C$_8$ alkyl, or —(C=O)R$^2$;
R$^9$ is —OR$^{10}$, —SR$^{10}$, or NR$^{10}$R$^{10}$;
R$^{10}$ is H, C$_1$-C$_6$ alkyl, —(C=O)R$^{11}$, unsubstituted phenyl, unsubstituted benzyl, or two R$^{10}$ groups joined to the same N may form a ring of 5 or 6 members containing up to two heteratoms chosen from O, S or N;
R$^{11}$ is H, C$_1$-C$_8$ alkyl, C$_2$-C$_8$ alkenyl, C$_2$-C$_8$ lakynyl, —CF$_3$, or unsubstituted phenyl, benzyl, or phenethyl;
R$^{12}$ is R$^2$ or halogen;
m and m′ are independently 0-8;
n and n′ are independently 0 or 1;
p and p′ are independently 0-8;
m+n+p is 1-10;
m′+n′+p′ is 1-10; Q$^1$ and Q$^2$ are independently —COOR$^2$, tetrazole, —CONHS(O)$_2$R$^{11}$, —CN, —CONR$^{10}$R$^{10}$, —CHO, —CH$_2$OH, —COCH$_2$OH, or —NHS(O)$_2$R$^{11}$;
X$^1$ is O, S, —NR$^2$, or —CR$^2$R$^2$—;
Y is —CR$^2$=CR$^2$—, —C≡C—, —CR$^2$R$^2$—X$^1$—, —X$^1$—CR$^2$R$^2$—, —CR$^2$R$^2$—X$^1$—CR$^2$R$^2$—

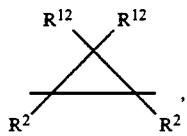

C=O,

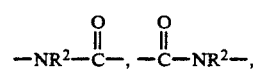

O, S, or —NR$^2$; and
Z$^1$ and Z$^2$ are independently 13 CONR$^2$—.

2. A process for synthesizing optically resolved compounds of Formula I which comprises
   (1) separating the diastereomers of compound III, when R$^{4'}$ is chiral, and
   (2) reacting a diastereomer of III with an appropriate electrophile.

* * * * *